(12) United States Patent
Benedetti et al.

(10) Patent No.: US 9,442,055 B2
(45) Date of Patent: Sep. 13, 2016

(54) PROCESS AND APPARATUS FOR THE MEASUREMENT OF THE HARDNESS AND FOR THE SELECTION OF AGRICULTURAL PRODUCTS

(75) Inventors: Luca Benedetti, Savarna (IT); Enrico Macrelli, Lugo (IT); Aldo Romani, Lugo (IT); Rudi Paolo Paganelli, Lugo (IT)

(73) Assignee: UNITEC S.P.A., Lugo (IT)

( * ) Notice: Subject to any disclaimer, the term of this patent is extended or adjusted under 35 U.S.C. 154(b) by 334 days.

(21) Appl. No.: 14/001,400

(22) PCT Filed: Mar. 22, 2012

(86) PCT No.: PCT/EP2012/055125
§ 371 (c)(1),
(2), (4) Date: Aug. 23, 2013

(87) PCT Pub. No.: WO2012/136484
PCT Pub. Date: Oct. 11, 2012

(65) Prior Publication Data
US 2013/0333454 A1    Dec. 19, 2013

(30) Foreign Application Priority Data
Apr. 5, 2011 (IT) .................. PN11A0022

(51) Int. Cl.
*G01N 3/40* (2006.01)
*G01N 3/30* (2006.01)
*G01N 33/02* (2006.01)

(52) U.S. Cl.
CPC *G01N 3/40* (2013.01); *G01N 3/30* (2013.01); *G01N 33/025* (2013.01); *G01N 2203/001* (2013.01); *G01N 2203/0051* (2013.01); *G01N 2203/0076* (2013.01)

(58) Field of Classification Search
CPC ............. G01N 33/025; G01N 2203/0051; G01N 2203/0076; G01N 2203/0082; G01N 2203/0623; G01N 3/40
USPC ........................................ 73/81, 83
See application file for complete search history.

(56) References Cited

U.S. PATENT DOCUMENTS

| | | | | |
|---|---|---|---|---|
| 2,277,037 A | * | 3/1942 | Clark | G01N 29/12 209/599 |
| 5,372,030 A | * | 12/1994 | Prussia | A61B 3/165 209/509 |
| 5,691,473 A | * | 11/1997 | Peleg | G01N 3/32 209/599 |
| 5,811,680 A | * | 9/1998 | Galili | G01N 3/38 73/12.01 |
| 5,918,266 A | * | 6/1999 | Robinson | G01N 3/12 209/599 |

(Continued)

Primary Examiner — Freddie Kirkland, III
(74) Attorney, Agent, or Firm — Birch, Stewart, Kolasch & Birch, LLP

(57) ABSTRACT

Method for measuring the hardness of agricultural products includes: implementing a test program suitable for identifying and selecting one or more indices (S3, S4) which can be measured with a non-destructive test on a respective product/fruit, correlated with the hardness (Du) of the same product/fruit, measured by a respective penetration test; and calculating the coefficients that define the straight line representative of the linear correlation between said indices and the hardness for the respective product. The method is implemented with the operations of: applying on the product a dynamic force, preferably of impulsive type; detecting the mechanical reaction through at least a piezoelectric transducer capable of generating an electric signal based on the application or transmission of said dynamic force through the respective kiwi fruit; and analyzing said electric signal relative to the fruit.

5 Claims, 5 Drawing Sheets

(56) References Cited

U.S. PATENT DOCUMENTS

| | | | | |
|---|---|---|---|---|
| 6,435,002 B1* | 8/2002 | Briggs | G01N 33/025 | 422/82.09 |
| 6,539,781 B1* | 4/2003 | Crezee | G01N 3/405 | 73/573 |
| 6,643,599 B1* | 11/2003 | Mohr | G01N 3/42 | 702/108 |
| 6,998,559 B2* | 2/2006 | De Baerdemaeker | G01N 3/405 | 209/518 |
| 7,392,720 B2* | 7/2008 | Howarth | G01N 3/48 | 73/661 |
| 8,346,388 B1* | 1/2013 | Tritz | B07C 5/34 | 209/590 |
| 2003/0201209 A1* | 10/2003 | De Baerdemaeker | G01N 3/405 | 209/576 |
| 2011/0040504 A1* | 2/2011 | Liu | G01N 33/025 | 702/56 |
| 2013/0298651 A1* | 11/2013 | Johnson | G01N 3/40 | 73/81 |

* cited by examiner

PROCESS AND APPARATUS FOR THE MEASUREMENT OF THE HARDNESS AND FOR THE SELECTION OF AGRICULTURAL PRODUCTS

The present invention refers to an improved method and an apparatus for measuring and determining the hardness of an agricultural product which, together with other product parameters, defines in general terms the quality of the product in order to decide its final destination and use.

The term agricultural products as used herein comprises potentially all types of fresh agricultural produce, and therefore not only fresh fruit in general, such as, in particular, kiwi fruit and peaches, but also other fresh vegetable products, such as potatoes, melons and cantaloupes, tomatoes, etc.

As is well known, normally in developed markets fresh produce offered to the public is first subjected to one or more measurements or selections to evaluate the characteristics that define on the whole its overall quality.

Various methods have been conceived and are currently implemented to measure and evaluate the quality of such products, which can be expressed as the set of external characteristics, such as colour, shape, size and evenness that are visible on the surface, and their internal characteristics.

The latter concern essentially the degree of ripeness, the taste, the sugar content and the wholeness of the flesh.

However, if such internal characteristics are to be examined with a non-destructive test, they will have to be determined only indirectly, by correlating these characteristics with the results of appropriate examinations, tests and measurements.

The objective of the present invention is to provide a new, non-destructive method, and a relative apparatus, to measure and evaluate some internal characteristics of an agricultural product.

Some fundamental methods are known in the art for evaluating the characteristics of such types of products.

Patent WO 94/29715 discloses a method for testing the quality of a fruit by applying a dynamic force, such as a slight impulse, to the fruit itself, sensing its dynamic reaction by means of a piezoelectric transducer supported by a suitable support means, so that the piezoelectric element is subjected to a reference load, and generating, as a reaction, an electric signal from said piezoelectric transducer corresponding to the speed of change of said load, and finally analyzing said signal and comparing it with the reference values for the purpose of determining the quality of the relative product.

Although this method is valid from the theoretical point of view, it has however shown to be scarcely reliable when applied as a method for determining, by correlation, the value of a quantity used in the most general sense to evaluate the quality of a fruit, like in particular the relative hardness.

Substantially, therefore, the invention described in said patent does not provide any practical teaching that is useful to process advantageously the data produced by the same method.

Moreover, said method has also shown itself scarcely reliable for the measurement on a massive scale of a large quantity of products.

Patent WO 97/27006 discloses a method for testing the quality of a fruit by applying a dynamic force, such as a slight impulse, to the fruit itself. This method is similar to the foregoing one, but it proposes an apparatus for imparting a dynamic force to the product to be tested, and for sensing a relative output signal by means of a piezoelectric transducer.

Although that method avails itself of improved mechanical/electrical means for testing the product, it too however completely lacks any real and effective teaching to correlate an electrical quantity sensed at an inherent characteristic of the examined product, and therefore it presents the same main inconvenient as the previous patent.

It would therefore be desirable, and it is the main objective of the present invention, to realize a type of procedure for measuring and evaluating a characteristic of an agricultural product on the basis of a correlation between:

the value of said characteristic,
and an index built on values of the electrical reaction of said product when it is subjected to a dynamic force, wherein said reaction is detected by piezoelectric means.

In a more specific and practical manner, the aim is to evaluate if a characteristic of the fruit being examined is included within predetermined values; according to the present invention, the characteristic considered is the hardness of the fruit, measurable with the penetrometer test.

The objective of the invention is to determine an index, measurable on the same product, that is correlated in a sensitive manner with the respective hardness, but that is measurable with a non-destructive test, unlike what occurs with the penetrometer test.

Thus it will be sufficient to "compare" with said index the extreme acceptable values of hardness, correlated to the same; in other words, the extreme values of hardness are assumed, and with the correlation already obtained are determined the extreme values of the interval of the corresponding index; it ensures that the values of the index of reference, that is measured for each fruit, are compared with said interval of the index, and the subsequent selection of the product is made on the basis of the result of said comparison.

This objective is achieved by a method implemented in accordance with the appended claims.

Characteristics and advantages of the invention will become evident from the description which follows, by way of non-limiting example, with reference to the enclosed drawings, wherein.

Figure 1:
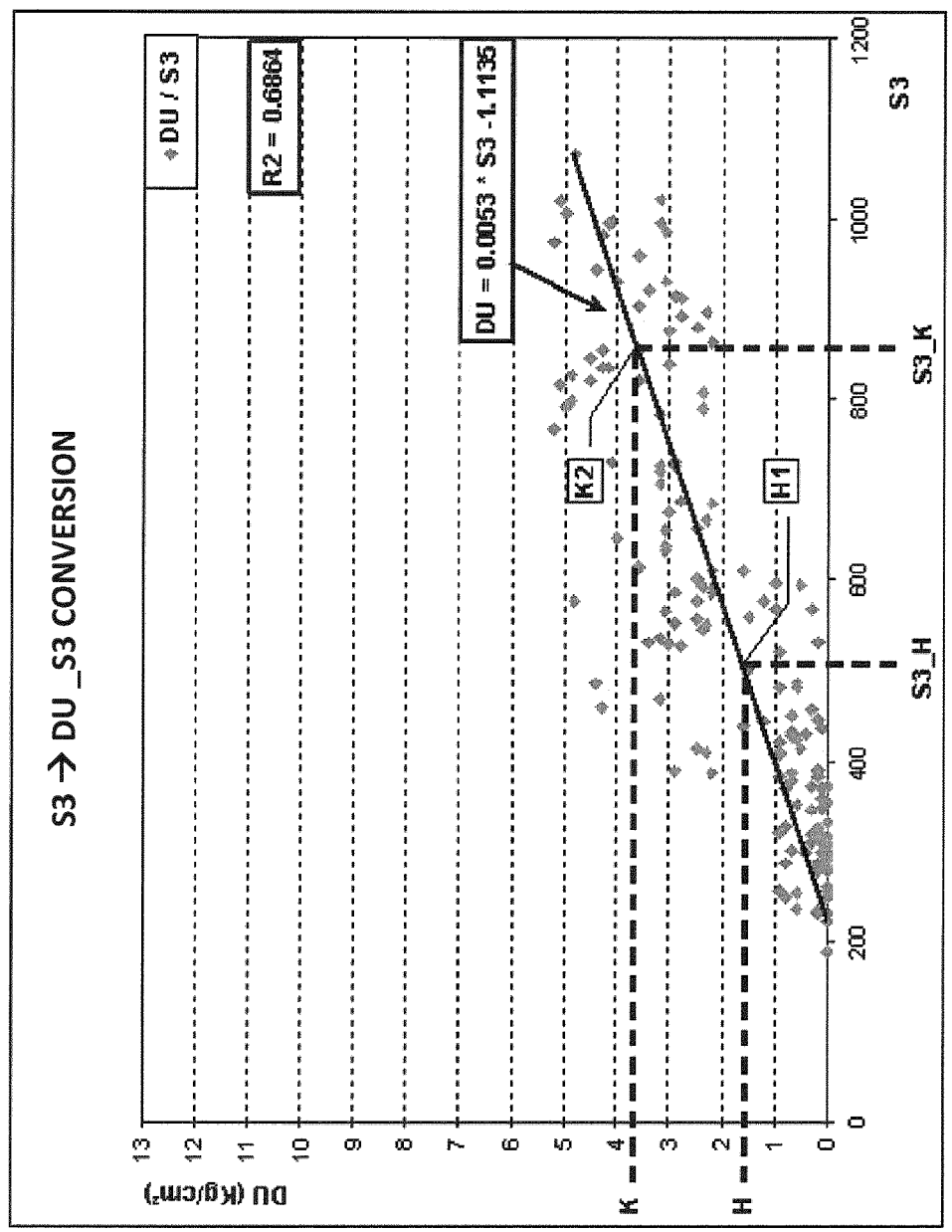
FIG. 1 shows a Cartesian plane in which are marked the points having coordinates corresponding to two correlated variables measured and detected in a first part of the experiment according to the invention.

Although the present invention refers specifically to a process, for a clearer explanation reference will however be made to a typical test cycle and to the relative devices with which said process can be carried out.

Moreover, for an easier and uncomplicated comprehension of the invention, in the following description it will be assumed that the external size of the product to be measured, along the course of propagation of the mechanical impulse, in other words between two piezoelectric electrodes arranged on opposite sides of the product to be measured, is already exactly known and therefore outside the scope of the present invention; in fact, the measurement of an external dimension of the fruit requires a completely self-evident and immediately applicable technique and therefore, for the sake of simplicity, hereunder it will be assumed that such dimension is already well known.

The agricultural products, and in particular the fresh fruit bound for consumer markets, before being sent to the various markets must satisfy precise characteristics and requirements which, as every operator knows, are typical for each type of market and use.

Essentially, said characteristics of the products considered together determine what, in general terms, is defined as their "quality".

Therefore, before they are sent to the intended markets, such products are generally picked and selected on the basis of those characteristics which together determine "quality"; thus, for each of said characteristics is first defined a respective acceptance range (usually expressed in quantitative terms, so as to allow the use of automatic measuring means), and finally said products are subjected to the measurement of the preselected characteristics.

Finally, based on the comparison between said acceptance range and the result of the respective measurements, the products are selected and sent to the various markets or uses, depending on the result achieved, that is, on the basis of their "quality". Among the various measurements carried out, one of the most important and representative of their general condition, in particular for the purposes of their destination and uses, is the test of the hardness of the internal flesh.

In fact, a universally known and accepted consideration, also based on common experience, and not only for experts in the field, is that the hardness of a fruit is one of the most important parameters to classify it and, most importantly, to decide its destination and use.

This parameter, or hardness, is measured with a method and a testing means that consist essentially of the so-called "penetrometer" test. This test is universally known among experts in the field; it will be sufficient to explain here that it consists of a hardness test of classical type, that is, consisting of:
  applying a tool with a probe having a cylindrical shape, of known area and, not irrelevant,
  pressing said probe orthogonally to the surface of the fruit or product, at the point of contact;
  exerting a sufficient pressure until said probe penetrates into the product being examined down to a predefined depth;
  measuring the force that is exerted on said probe to reach said predefined depth.

The value of the force thus measured, defined as "hardness" and represented by the symbol "Du", supplies a conventional value of hardness of the product that, as mentioned above, is strictly correlated and thus representative of the degree of ripeness of the product.

This test, in general very valid and easily carried out with simple and immediate means and procedures, presents however the insurmountable problem of being a destructive test, so that the product or products that were subjected to the test cannot be considered whole, because they are obviously damaged; therefore, this test can only be carried out on a small sample of products.

The final consequence is that this test, since it can be carried out on a sample of products, often is not representative of the average quality of the lot from which the product is drawn. Still worse, given the generally high variability of characteristics of products from the same lot, there may be products that are absolutely unacceptable, but that would be automatically accepted because they are included in a lot whose average "quality" has been evaluated and considered acceptable.

This situation is completely unwelcome and dangerous from the commercial point of view.

To overcome this problem, the present invention has set the objective of identifying one or more other parameters or "indexes" that could:
  provide, if necessary together with other parameters, a reliable indication of the general condition of the product, and therefore that could be correlated with the characteristic measurable with the above-mentioned "penetrometer" test;
  be absolutely non-destructive;
  be implemented on an industrial scale, with means known in the art.

The present invention is thus the result of a wide-ranging series of trials and tests to identify said indicators and the relative testing means and procedures.

Obviously, the details of such program of tests are not provided, both because they also include all the tests that have not led to useful results, and because what applies here is only to bring the final results that can be used to disclose, in a precise and detailed manner, the teaching necessary and sufficient to implement a valid, verifiable and repeatable testing method.

For the purpose of better supporting the contents of the invention, and of documenting the experiment that has led to this invention, this is illustrated hereafter in detail.

1) The Experiment:

The experiment consisted in verifying and measuring the existing correlation between the following parameters/indexes:

Index S3
  concerning hardness, represented here with the symbol "Du" (penetrometer test).

Evidently, on the basis of what was mentioned above, each fruit first underwent the measurement of its S3 index, after which it was put through the penetrometer test.

1A) This first S3 index is defined as follows:

$$S3=(\Delta l/\Delta t)^2$$

where $\Delta l$ is the length of the path of a dynamic impulse that crosses the product or fruit being examined, measured from the point at which such force is applied to the point where such force is detected, and $\Delta t$ is the crossing time of said dynamic force through the fruit.

The testing procedure and the means used to detect $\Delta t$ will be explained later. It is sufficient at this time to specify that this data represents the time elapsed, in milliseconds;
  from the moment when a dynamic, that is, mechanical, force is imparted on the product, or fruit, being examined, on a delimited area of its surface and crosses the same fruit along a path of $\Delta t$ length;
  until the moment when such force is detected, in another area of its surface, preferably in the area opposite the one in which it was applied.

In practice, and very briefly, this means impacting the fruit lightly from one side, and measuring the speed of propagation of said impact inside the fruit.

$S3=(\Delta l/\Delta t)^2$ is thus the square of said propagation speed.

1B) Index of Hardness

The meaning of the measurement of the hardness (Du) has already been explained above, and thus for the sake of brevity it is not repeated here.

1C) Fruit Subjected to the Experiment: Lot of Kiwi Fruit;
1D) Instrument for Measuring Hardness:

In the present experiment, reference is made to a Model FT327 penetrometer supplied by the firm TR Snc, with headquarters in Via Copernico 26 (47100) Forlì (Italy), also shown in their site www.trsnc.com.

Figure 5:
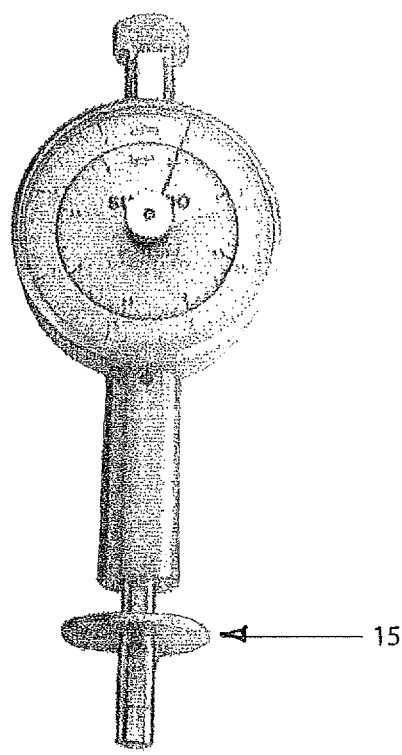
FIG. 5 is a general external view of the tool used to measure the hardness of the fruit in general.
Figure 6:
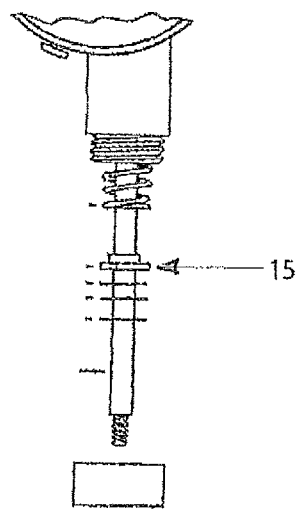
FIG. 6 is a simplified diagram, in external orthographic projection, of the measuring rod of the tool of FIG. 5.

The penetrometer model used in the experiment is also shown in FIGS. 5 and 6, and uses a probe of cylindrical type with a reference ring and a stop 15, and having a circular penetration cross section of 8 mm diameter.

This feature is essential to implement the invention; in fact, the measurement of the penetration force measures in reality the pressure necessary to insert the probe into the fruit for a predetermined depth.

Thus, if a probe with a different area of penetration, for example double, is used, then it would naturally be necessary to apply a penetration force twice as large to obtain the same depth of penetration, because what is really to be measured is not the force of penetration but the resistance of the fruit to a given penetration pressure.

But since the pressure in itself is a quantity that is not directly measurable, at least in the case under consideration, it is necessary to determine the value of such quantity indirectly, and therefore, as the pressure is the result of a force divided by the relative area of application of such force, it follows that, in the case under consideration, the values of the force measured by the penetrometer must always be ascribed to the penetration section of the relative probe.

1E) Implementation of the Experiment

The experiment consisted in verifying the existence and the extent of the correlation between the two indices, hardness (Du) and S3, that can be detected on the same fruit.

For the specific purpose, the experiment consisted in subjecting the individual fruits to the separate measurement of two different indices, that is:
index S3,
and the respective hardness test "Du",
and then statistically analyzing the results.

Statistical Analysis

Statistical analysis was carried out between the S3 and Du values.

The statistical analysis of correlation between two series of numbers (each of which being representative of the value of a quantity) is a type of universally known classical analysis, and thus its explanation is omitted.

It suffices to point out that it is stated that two variables are correlated when a significant correlation can be demonstrated between a double series of corresponding values (such as for example S3 and Du) that vary jointly, without there being a direct cause-effect relationship between them, but when both are tied for example to a third variable.

To measure this correlation, the statistical index $R^2$, called "linear correlation coefficient", is used; this is well known in classical statistical analysis, and thus will not be illustrated further.

This index is obtained from the relationship between the covariance and the product of the two variances of the two variables being examined (S3 and Du); this index can be positive or negative, and may vary from zero to one; it is maximum, equal to one, when there is a perfect linear correspondence between the two variables (that is, their correlation is represented on a Cartesian plane by a straight line) and it is minimum, equal to zero, when there is no correlation.

In processing values, naturally referring to the respective kiwi fruit, for the purpose of verifying a possible correlation, it was found that:

a) the correlation coefficient between the two variables -S3- and -Du- is $R^2=0.6864$, and therefore an index that demonstrates a good linearity relationship between the two variables being examined.

b) the values of the coefficients $\underline{a}$ and $\underline{b}$ of the linear correlation straight line, represented by the general function: $Y=b \cdot x+a$, turned out to be:
a=−1.1135 and b=0.0053.

Therefore, the correlation straight line between the values-indices, both measured, of Du and S3 becomes $$Du=0.0053 \cdot S3-1.1135.$$

To show the positioning of said straight line with respect to the values (and therefore the individual fruits) that generated it, the line was drawn in the Cartesian plane of FIG. 1. In said FIG. 1 is also shown a large set of points having coordinates of hardness -Du- (in ordinate) and of the index S3 (in abscissa), each of said values being measured and calculated for respective kiwi fruits.

On the same plane is also plotted the correlation straight line "R" defined above.

In short, it has been demonstrated that:
the values of hardness "Du" and of S3 are highly correlated, and that
the relative correlation straight line is indicated as: Du=0.0053·S3−1.1135.

After having identified the coefficients a and b, the problem at the base of the invention is virtually resolved; in fact, it will be sufficient to proceed according to the classical method, that is:
introduce in the previous relationship the value of the known variable, which in our case is the value of S3, and then to calculate the value of the unknown variable, that is, "Du", the searched hardness value, which thus is determined indirectly.

Determination of Index S3

Figure 2:
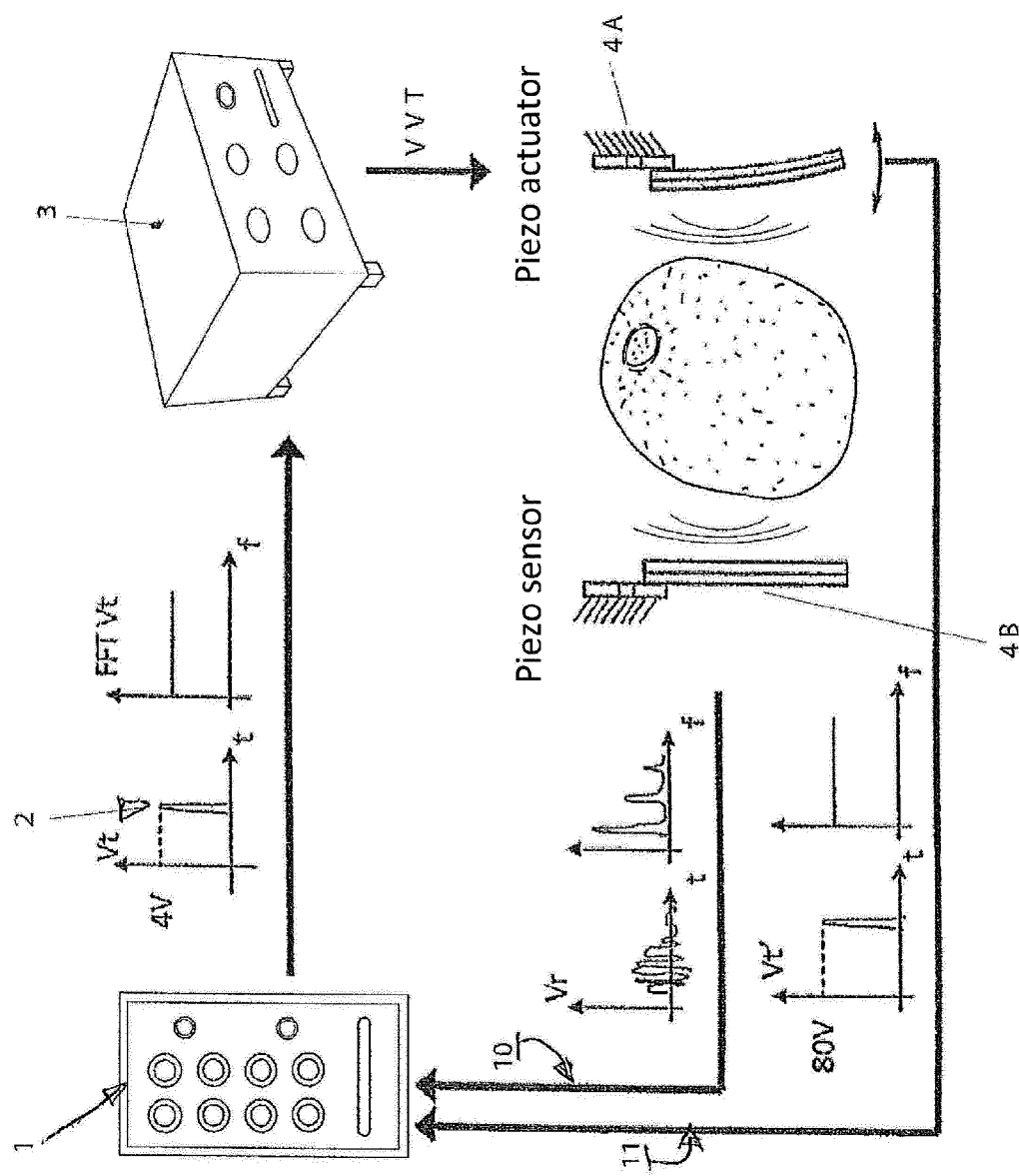
FIG. 2 illustrates the overall testing circuit used in the experiment of the invention.
Figure 3:
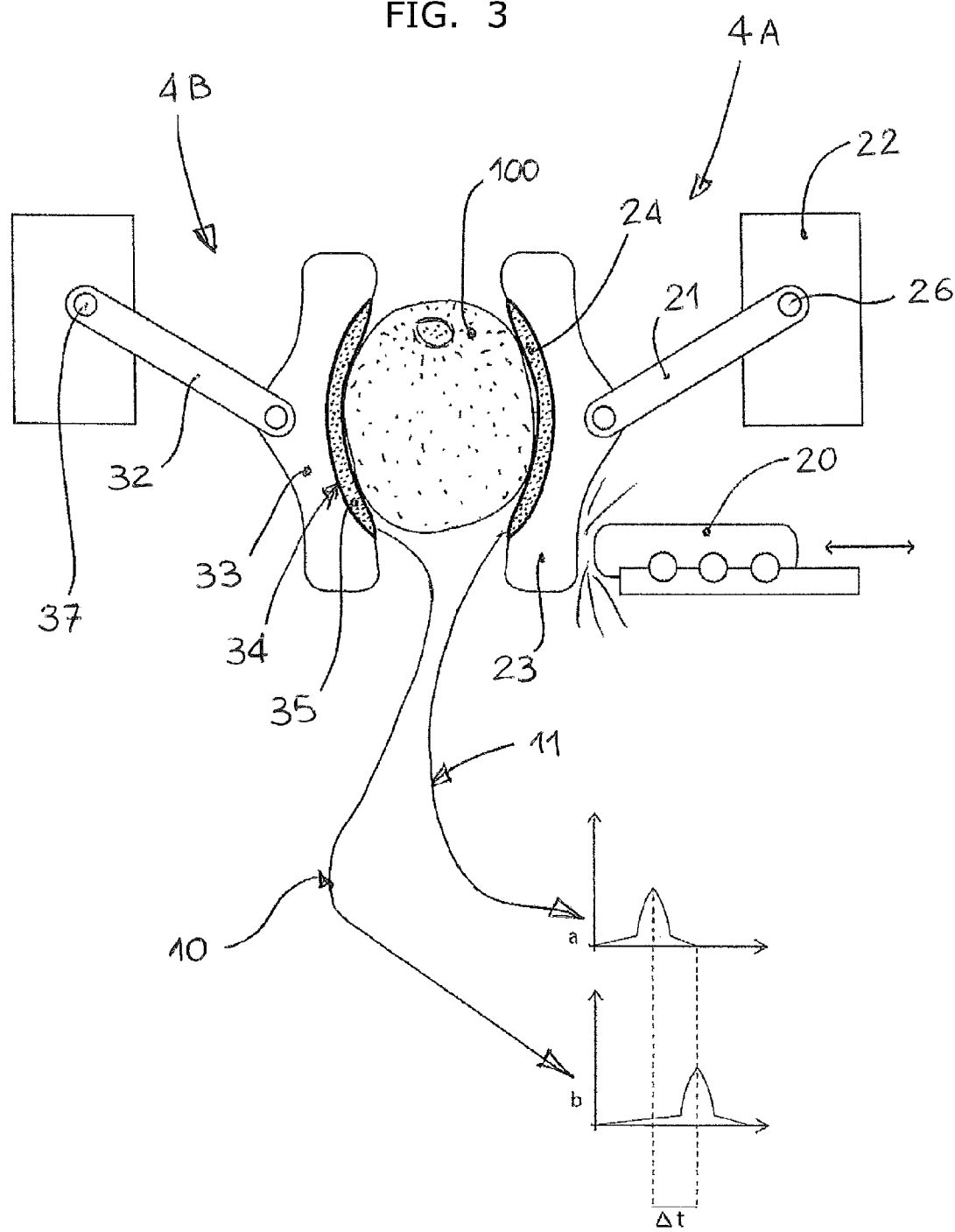
FIG. 3 illustrates a detail of the circuit of FIG. 2.

To determine the value of index $S3=(\Delta l/\Delta t)^2$ for each kiwi fruit, a measuring device shown in FIGS. 2 and 3 can be used.

FIG. 2 illustrates the block diagram of a complete circuit for measuring the S3 value.

Said circuit includes:
an pulse generator 1 that transmits a sequence of pulses 2 consisting of a half cycle of a sinusoidal wave Vt to a power amplifier 3; in this step, said pulses can be processed in various manners, not disclosed here, to make them more usable and more detectable in the continuation of the process.

Said power amplifier 3 generates a power signal VVT that feeds a device of essentially piezoelectric nature that includes a section 4A for generating a dynamic force, that can also be of impulse type, and a subsequent section for receiving the relative dynamic impulse 4B.

The signal Vr received by said section 4B, after being processed in turn, is sent to a first receiving channel 10, which is designed here in an integrated manner with the impulse generator 1.

In addition, the same power signal too is sent to a second receiving channel 11, functionally associated with said first receiving channel 10.

Said two signals are thus received in two instants very close to each other, but not coincident.

In fact, the signal on channel 10 is obviously delayed with respect to the signal on channel 11 due to the fact that it had to cross the fruit being examined, and the relative mechanical propagation naturally requires a definite time, because it is transmitted at a finite speed.

At this point, the delay time between said two signals on channels 10 and 11 is measured to obtain the value of the Δt variable in the relation: $S3=(\Delta l/\Delta t)^2$.

The second variable Δl represents, as already mentioned, the distance between the transmission zone and the receiving zone of the mechanical impulse through the fruit.

This data is thus a simple measurement of a distance between two well-defined external points of the fruit; thus, it is a completely self-evident measurement of the geometrical length that does not require any particular teaching, and for this reason there is no need to illustrate it further.

For what concerns the composition and the manner of operation of said two sections 4A and 4B, FIG. 3 illustrates a preferred embodiment.

The dynamic force is generated with known methods, as for example a lever with controlled operation 20, or an equivalent device that impresses a controlled mechanical force, transmitted to an arm 21 that is hinged, at one end, to a fixed part 22, and at the other end to a support, preferably elastic and concave 23.

On the surface of said concavity, on which is applied the fruit to be examined, is arranged a transducer piezoelectric film 24.

Opposite this first section 4A is arranged a second section 4B that includes a set substantially similar to the previous one, in other words a second arm 32 holding a concave support 33 on the concave surface of which 34 is similarly arranged a second piezoelectric transducer film 35.

Said second support 33 is in turn connected to one end of the arm 32 the opposite end of which is hinged at a fixed point through a relative pin 37.

The fruit 100 is held and supported between the two concave surfaces of the supports 23 and 33, and in particular between the respective piezoelectric film 24 and 35.

It is thus evident that, if any mechanical force is applied to the fruit 100, this force is transmitted through one of said supports and the relative piezoelectric film, and the same force is transmitted, through the entire fruit, to the opposite piezoelectric film, naturally at its own specific speed.

Thus, if said first reception channel 10 is connected to said first transducer 24, and the second reception channel 11 is connected to said second transducer 35, it will be readily seen that said two channels 10 and 11 are crossed by relative signals that represent a similar physical phenomenon, in other words the mechanical force applied to the fruit, but this phenomenon is detected at two different instants (one later than the other), that correspond to the precise instant in which the same force reaches one or the other piezoelectric film, 24 and 35 respectively.

Thus, said delay between the two signals measures exactly the transmission time of the mechanical impulse through the fruit 100, and the problem presented is thus resolved.

A person skilled in the field will have understood that what is presented above in a simplified manner is only one of the many methods of measuring the crossing time of an impulse through a fruit; since such methods are already well known, their further illustration is omitted.

At this point, having obtained the straight line Du=0.0053·S3−1.1135 of FIG. 1, the solution of the problem at the basis of the invention can be readily obtained.

The problem presented is in fact to determine if a characteristic of the fruit being examined falls within the preset values; according to the present invention, the characteristic considered is the hardness of the fruit, measurable with the penetrometer test.

The objective of the invention is to determine an index, measurable on the same product, that can be correlated significantly with the respective hardness, but that is measurable with a non-destructive test, unlike what happens with the penetrometer test.

Therefore, it will suffice to "compare" with this index the extreme acceptable values correlated to it; that is, the extreme values of hardness are taken, and with the correlation already obtained the extreme values of the interval of the corresponding index are determined. It follows obviously that the values of the referred index, measured for each fruit, are then compared with said interval of the index, and the subsequent selection of the product is carried out on the basis of the results of said comparison.

Thus, on this basis it will be sufficient, referring again to FIG. 1, to mark on the axis of the abscissas, or of the hardness value -Du- as measured by the penetrometer, the two extreme values H and K of the predetermined interval of acceptability, and then to project on the straight line Du=0.0053·S3−1.1135 the corresponding points H1 and K2, and finally to project these points on the axis of the ordinates, that is of the index S3, and to find the extreme values of the interval of the same index S3_H, S3_K.

Then, as in all the selections, the fruit is evaluated and selected in one sense or the other, depending on the value of the respective index S3 with respect to said interval S3_H, S3_K.

It was also tested and ascertained that a particularly advantageous solution, taking into account the real business environment, and the statistical and technical nature of the tests, is attained if the parameters a and b can vary individually within a tolerance of 15%, independently of the chosen value, and therefore independently of the tolerance of the other coefficient with respect to the relative nominal value.

In the course of long and wide-ranging experiments, carried out exactly with the same methods and means previously described, it was found that there is also a second index, measured on the kiwi fruit, significantly correlated with its hardness measured as explained above.

This second index is:

$$S4 = m/(\Delta l \cdot \Delta t^2)$$

with m=weight of the fruit in grams.

Δl=length of the fruit, in millimeters, in the section crossed by the mechanical impulse;

Δt=crossing time of the same impulse, in milliseconds

For what concerns the "new" variable m, that is, the weight of the fruit, in this case too it is evident that its measurement is self-evident and immediate, and therefore it will not be explained further.

This second index is obtained from a wide-ranging series of tests and measurement generated from a type of experiment substantially identical to the previous one.

The tests and conditions of the experiment that led to the identification of said second index S4, and that verified its high significance, could be explained hereinbelow. However, since the considerations to make, and the test conditions are identical to those considered for the S3 index, for the sake of simplicity and conciseness their repetition is omitted.

Figure 4:
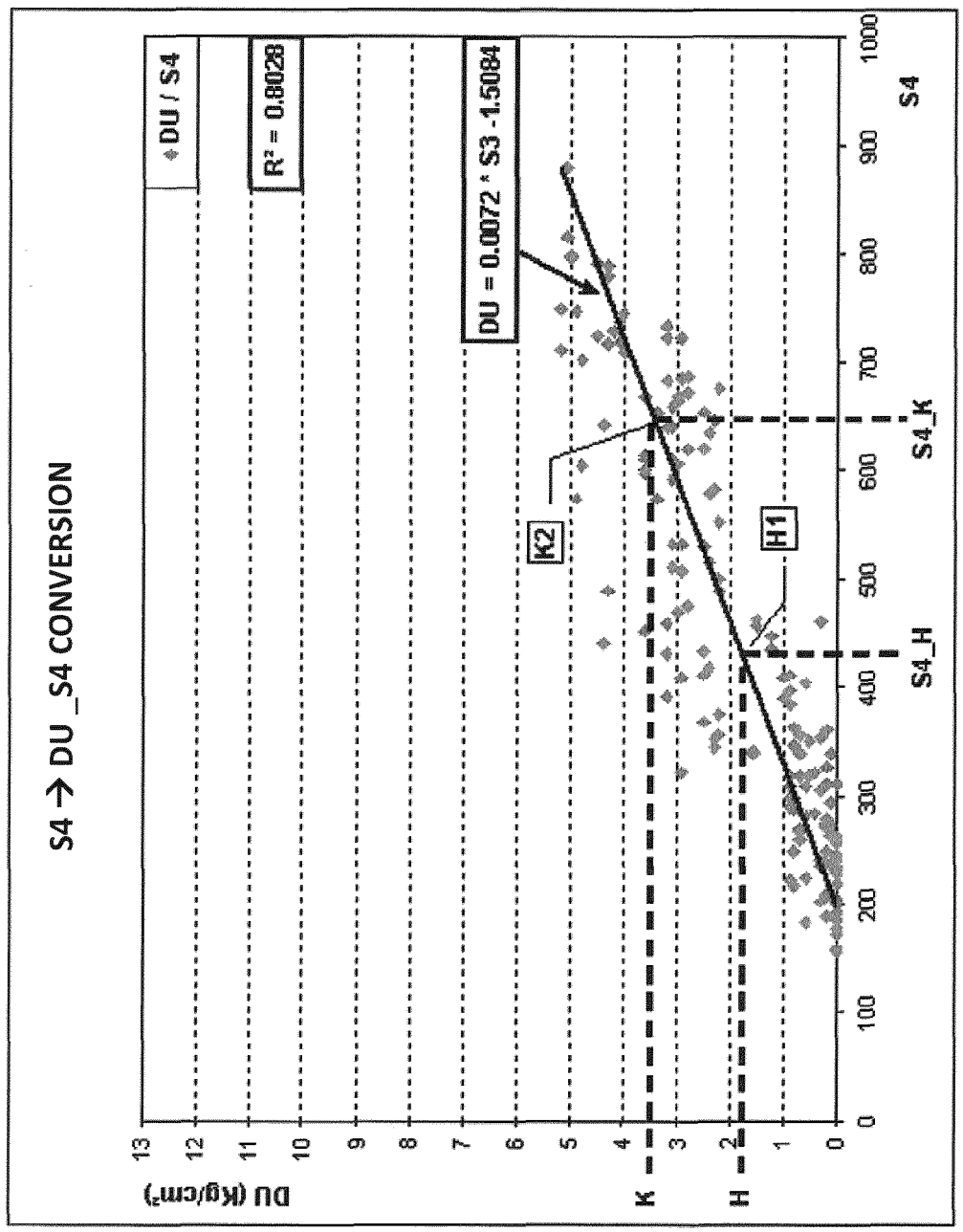
FIG. 4 shows a Cartesian plane in which are marked the points having coordinates corresponding to two other correlated variables detected in a second part of the experiment according to the invention.

In addition, FIG. 4 illustrates, similarly to FIG. 1, the position of the individual points having coordinates (Du, S4), with -Du- in the ordinate showing the numerical value of the hardness of each kiwi fruit tested.

In the present case too, similarly to what is illustrated in FIG. 1, the present FIG. 4 shown on a Cartesian plane the relationship that exists between the measured hardness values, arranged in the abscissa (Du), and the corresponding S4 values.

In this case too their correlation is clearly evident, and it is also marked by the relative correlation straight line.

In the present second experiment, it was found that:
a) the correlation coefficient between the two variables S4 and Du is $R^2=0.8028$, that is, an index that demonstrates an excellent relationship of linearity between the two variables examined;
b) the values of the coefficients $\underline{a}$ and $\underline{b}$ of the linear correlation straight line, represented by the general function $Y=b \cdot x_+ a$ were: $a=-1.5084$ and $b=0.0072$.

Thus, the straight line of correlation between the values-indices of Du and S4 becomes:

$$Du=0.0072 \cdot S4-1.5084.$$

To show the positioning of said straight line with respect to the values (and thus to the individual fruits) that generated it, the line was drawn on the Cartesian plane of FIG. 4; in said FIG. 4 is also plotted a large series of dots having coordinates -Du- and S4, each of said values being measured and calculated for respective kiwi fruits.

In short, it was shown that:
the values of "Du" (hardness) and S4 are highly correlated, and that:
the relative correlation straight line is represented as follows:

$$Du=0.0072 \cdot S4-1.5084.$$

It will again be evident that, once the present correlation straight line is determined, that the manners of selecting the fruit according to said second index S4 are in all ways similar to those previously illustrated in the case of index S3, and in particular, with reference to FIG. 4, to the relative intervals $H \ggg K$ and $S4\_H \ggg S4\_K$.

And in addition, also in the present case, it was ascertained that a particularly advantageous solution, taking into account the real commercial environment, and the statistical and technical nature of the tests, is attained if the parameters $a=-1.5084$ and $b=0.0072$ can also vary individually within a tolerance of 15%, independently of the chosen value, and therefore independently of the tolerance of the other coefficient with respect to the relative nominal value.

The invention claimed is:

1. A method for determining hardness of an agricultural product, comprising:
    measuring a weight (m) of the agricultural product;
    applying to said agricultural product a dynamic force through a first piezo-electric transducer configured to generate a first electric signal corresponding to application of said dynamic force;
    detecting a dynamic reaction of said agricultural product through a second piezo-electric transducer configured to generate a second electric signal corresponding to transmission of said dynamic force through said agricultural product;
    analyzing said first and second electric signals correlated to the hardness of said agricultural product, and measuring said crossing time ($\Delta t$) and said path length ($\Delta l$) of said dynamic force through said agricultural product;
    calculating an index S4 from $S4=m/(\Delta l \cdot \Delta t^2)$; and
    determining the hardness (Du) of the agricultural product based on the calculated index S4 and a linear correlation $Du=b \cdot S4+a$,
    where a and b are coefficients defining the linear correlation between a respective hardness (Du) and a respective index S4 measured on a respective agricultural product, and
    wherein the respective hardness (Du) was calculated from a penetrometer hardness test performed on the respective agricultural product and the respective index S4 was calculated from a non-destructive test comprising measurement data, detected by at least a piezo-electric transducer, of at least the crossing time ($\Delta t$) and the length of a path ($\Delta l$) of a dynamic force applied to and crossing through said respective agricultural product and measurement data of a weight of the respective agricultural product.

2. Method according to claim 1, wherein the agricultural products is a kiwi fruits, and said coefficients (a, b) of said linear correlation ($Du=b \cdot S4+a$) are respectively:
    $b=0.0072$ and $a=-1.5084$.

3. Method according to claim 2, wherein the numerical values of said coefficients (a, b) show an independent tolerance of $\pm 15\%$.

4. Method according to claim 1, wherein said dynamic force applied to said agricultural product is of an impulse type.

5. Method according to claim 1, wherein said first and second piezo-electric transducers are arranged, in use, at opposite portions of the agricultural product.

* * * * *